United States Patent

Sekine et al.

[11] Patent Number: 5,968,899
[45] Date of Patent: Oct. 19, 1999

[54] MEDICINAL COMPOSITIONS OF PEPTIDES WITH EACA OR TRANEXAMIC ACID FOR ENHANCED MUCOSAL ABSORPTION

[75] Inventors: Takashi Sekine; Kazuyuki Ishikawa; Takayoshi Kimura; Yoshinobu Nakai, all of Ami-machi, Japan

[73] Assignee: Tsumura & Co., Tokyo, Japan

[21] Appl. No.: 08/737,930

[22] PCT Filed: Jun. 2, 1995

[86] PCT No.: PCT/JP95/01085

§ 371 Date: Dec. 2, 1996

§ 102(e) Date: Dec. 2, 1996

[87] PCT Pub. No.: WO95/33474

PCT Pub. Date: Dec. 14, 1995

[30] Foreign Application Priority Data

Jun. 3, 1994 [JP] Japan .................. 6-145605

[51] Int. Cl.$^6$ .............. A61K 38/17; A61K 38/09; A61K 38/10; A61K 38/16

[52] U.S. Cl. ............. 514/3; 514/2; 514/8; 514/12; 514/21; 514/802

[58] Field of Search ................ 514/3, 12, 21, 514/2, 8, 946, 964, 802

[56] References Cited

U.S. PATENT DOCUMENTS 5,578,324 11/1996 Dohi et al. ..................... 424/499

FOREIGN PATENT DOCUMENTS 0667163 8/1995 European Pat. Off. .

OTHER PUBLICATIONS

Tau et al., Biomaterials, vol. 14 (11), p. 823–833, 1993.
Pluromic (Information Brochure), Wyandotte Chem. Corp., pp. 1–14, 1952.
Pec et al., J. Pharm. Sci., vol. 81 (7), p. 626–630, 1992.
The United States Pharmacopeia, 16$^{th}$Edn, pp. 1491–1493, 1985.
Parsons et al., Br. 13 J. Pharm., vol. 66, pp. 25–32, 1979.
Manning et al., Pharm. Res., vol. 6 (11), pp. 903–918, 1989.
Johnston et al., Pharm. Res., vol. 9(3), pp. 425–434, 1992.
Wang et al., J. Parenteral. Sci & Tech., vol. 42(2s) p. S3 to S26, 1988.
Duncan et al., Int. J. Pharm., vol. 120, pp. 179–188, 1995.

*Primary Examiner*—Chhaya D. Sayala
*Attorney, Agent, or Firm*—Oblon, Spivak, McClelland, Maier & Neustadt, P.C.

[57] ABSTRACT

Disclosed is a medicinal composition, which comprises a peptide as an effective ingredient and as bases, epsilon aminocaproic acid or tranexamic acid and an ethylene oxide-propylene oxide block copolymer represented by the following formula (I):

$$HO(C_2H_4O)_a-(C_3H_6O)_b-(C_2H_4O)_cH \qquad (I)$$

wherein a, b and c stand for integers of 1 or greater, respectively. According to this medicinal composition, the peptide can be absorbed at a high rate through the mucosa and further, its pharmacological effects are prolonged over for a long time.

22 Claims, No Drawings

MEDICINAL COMPOSITIONS OF PEPTIDES WITH EACA OR TRANEXAMIC ACID FOR ENHANCED MUCOSAL ABSORPTION

TECHNICAL FIELD

This invention relates to a medicinal composition, and more specifically to a medicinal composition which makes it possible to absorb a peptide, which is susceptible to decomposition and has a low absorption rate, at a high rate through a mucosa or the like and further to prolong its pharmacological effects over a long time.

BACKGROUND ART

Peptides have conventionally been employed for the treatment or the like of various diseases. For example, calcitonin, insulin, interferon and erythropoietin are used for the improvement of osteoporosis and pains associated with osteoporosis and the treatment of diseases such as hypercalcemia, for the treatment of diseases such as diabetes, for the treatment of diseases such as hepatitis and renal carcinoma, and for the treatment of diseases such as anemia, respectively.

As an administration method of peptides, administration by injection is usual because of the difficulty in having them absorbed through the digestive tract. However, this injection-reliant administration is not an administration method which permits self-administration by a patient, so that regular outpatient treatment is required. It also involves the problem of administration being accompanied by painful discomfort.

On the other hand, from the standpoint of economy, oral administration is accompanied by a problem because the absorption rate of a peptide through the digestive tract is low and moreover, the peptide is subjected to decomposition, first-pass effect and the like by proteinases and hence, the peptide has to be administered in a very large quantity to have it absorbed in an effective amount through the digestive tract.

Concerning the administration form of peptides, a great deal of research is now under way to overcome the above-described problems. Intranasal sprays containing peptides as effective ingredients have already been developed in Europe. However, they are accompanied by problems such as insufficient absorption of the peptides and are not satisfactory.

With a view to increasing the absorbability of peptides, it has heretofore been attempted to formulate them into preparations with the addition of a bile acid salt or a surfactant [Japanese Patent Application Laid-Open (Kokai) No. SHO 59-130820, Japanese Patent Application Laid-Open (Kokai) No. SHO 59-89619, and Japanese Patent Application Laid-Open (Kokai) No. SHO 63-39822] or to use a proteinase inhibitor for promoting permucosal absorption [J. Pharmacobiodin. 14(2), S4, 1991, and Japanese Patent Application Laid-Open (Kokai) No. HEI 3-48627). The absorption enhancers employed in these preparations are all accompanied by one or more safety problems such as excessively strong mucosal irritation, so that none of them have been put into practice.

From the foregoing circumstances, there is an outstanding desire for the development of a preparation which is free of the above-described problems.

DISCLOSURE OF THE INVENTION

With the foregoing circumstances in view, the present inventors have conducted extensive research with a view to developing a medicinal composition excellent in absorbability and safety despite its easily-applicable administration form. As a result, it has been found that the above object can be achieved by adding a peptide to a base containing epsilon aminocaproic acid or tranexamic acid and an ethylene oxide-propylene oxide block copolymer represented by the below-described formula (I), leading to the completion of the present invention.

Namely, an object of the present invention is to provide a medicinal composition comprising a peptide, epsilon aminocaproic acid or tranexamic acid, and an ethylene oxide-propylene oxide block copolymer represented by the following formula (I):

$$HO(C_2H_4O)_a-(C_3H_6O)_b-(C_2H_4O)_cH \quad (I)$$

wherein a, b and c stand for integers of 1 or greater, respectively.

BEST MODES FOR CARRYING OUT THE INVENTION

No particular limitation is imposed on the peptide for use in the medicinal composition according to the present invention insofar as it is a peptide having pharmacological effects. Its specific examples can include calcitonin, insulin, proinsulins, epidermal growth factors, growth hormones, somatomedin C, somatostatin, granulocyte macrophage colony-stimulating factor, colony-stimulating factors, erythropoietin, interferons, interleukins, atrial natriuretic peptides, parathyroid hormones, superoxide dismutases, tissue plasminogen activators, antithrombins, blood coagulation-factor, blood coagulation-factor, protein C, hirudine, hepatitis vaccine, endorphins, ACTH-releasing hormone, neurotensin, angiotensin, transferrin, endothelin, vasopressin, desmopressin, luteinizing hormone, luteinizing hormone-releasing hormone, prolactin, glucagon, gastrin, secretin, urokinase, vasoactive intestinal polypeptide, hepatitis vaccine, influenza vaccine, pertussis vaccine, diphtheria vaccine or tetanus vaccine. Of these, preferred are calcitonin, insulin and the like. These peptides can be used either singly or in combination.

The ethylene oxide-propylene oxide block copolymer—which is employed in the medicinal composition according to the present invention and is represented by the following formula (I):

$$HO(C_2H_4O)_a-(C_3H_6O)_b-(C_2H_4O)_cH \quad (I)$$

wherein a, b and c stand for integers of 1 or greater, respectively (hereinafter called "EO-PO polymer (I)")—is generally specified by the average polymerization degree of ethylene oxide and the average polymerization degree of propylene oxide, in other words, by the sum of a and c (the average polymerization degree of ethylene oxide) and b (the average polymerization degree of propylene oxide) in the formula (I).

In one embodiment the ethylene oxide-propylene oxide block copolymer has an HLB of from 5 to 33. In another embodiment, the ethylene oxide-propylene oxide block copolymer has an HLB of from 10 to 30.

Any EO-PO polymer (I) is usable insofar as the above-described object can be attained. However, preferred is an EO-PO polymer (I) in which the average polymerization degree of ethylene oxide is from 10 to 200 and the average polymerization degree of propylene oxide is from 10 to 80. Specific examples can include
ethylene oxide (20) propylene oxide (20) glycol, ethylene oxide (25) propylene oxide (30) glycol,
ethylene oxide (160) propylene oxide (30) glycol,
ethylene oxide (54) propylene oxide (39) glycol,
ethylene oxide (196) propylene oxide (67) glycol,
ethylene oxide (200) propylene oxide (70) glycol,
ethylene oxide (42) propylene oxide (67) glycol,
ethylene oxide (44) propylene oxide (39) glycol, and
"Pluronic P103" (product of BASF Wyandotte Corporation).

Among these, EO-PO polymers (I) having an HLB of 13 or greater are preferred in order to fully attain the above-described object. Preferred specific examples can include ethylene oxide (20) propylene oxide (20) glycol, ethylene oxide (25) propylene oxide (30) glycol, ethylene oxide (160) propylene oxide (30) glycol, and ethylene oxide (54) propylene oxide (39) glycol, with ethylene oxide (20) propylene oxide (20) glycol, ethylene oxide (25) propylene oxide (30) glycol and ethylene oxide (160) propylene oxide (30) glycol being particularly preferred. These EO-PO polymers (I) can be used either singly or in combination.

Further, epsilon aminocaproic acid and tranexamic acid which are employed as additives in the medicinal composition according to the present invention are known medicines having antiplasminal effect. They are generally used as oral preparations or injections, so that such oral preparations or injections can be used.

A description will next be made about formulation of the medicinal composition according to the present invention into dosable preparations.

The medicinal composition according to the present invention can be prepared by combining the peptide, the EO-PO polymer (I), and epsilon aminocaproic acid or tranexamic acid together and, after adjustment of its pH as needed, adding appropriate additives and then forming the resultant mixture into a desired dosable preparation form in a manner known per se in the art.

As the amount of the peptide in the medicinal composition according to the present invention varies depending on the kind of the peptide, the administration form and the like, it is necessary to incorporate the peptide in an effective amount which varies with the kind of the peptide, the administration form and the like. This effective amount can be determined, for example, by an animal experiment and a clinical experiment while taking into consideration increases in its blood concentration. When calcitonin is used, for example, it is sufficient to incorporate it in an amount to give a dose of 0.01 to 10 IU/kg or so.

On the other hand, the amount of the EO-PO polymer (I) in the medicinal composition according to the present invention generally ranges from 0.01 wt. % to 20 wt. %, preferably from 0.1 wt. % to 10 wt. %, particularly preferably from 0.5 wt. % to 5 wt. %. An amount of the EO-PO polymer (I) smaller than 0.01 cannot bring about the desired effects, whereas an amount in excess of 20 wt. % may, depending on the preparation form, make it difficult to practice the present invention for an increase in the viscosity of the preparation or a like reason.

Further, the amount of epsilon aminocaproic acid or tranexamic acid in the present invention can preferably be from 0.01 wt. % to 10 wt. %, with a range of from 0.01 wt. % to 2 wt. % being particularly preferred. An amount of epsilon aminocaproic acid or tranexamic acid smaller than 0.01 wt. % cannot bring about the desired effects, while an amount greater than 2 wt. % may, in some instances, lead to difficulty in adjusting an osmotic pressure upon contact of the preparation with a mucosa. An amount of 10 wt. % or greater may result in a high osmotic pressure so that a mucosa may be dried in some instances.

Moreover, the pH of the medicinal composition according to the present invention can preferably be in a range of from 2 to 7 to minimize irritation to a mucosa.

The medicinal composition according to the present invention can be formulated into conventionally-known various preparation forms. Examples include intranasal preparations (sprays, nasal drops and the like), aerosols, rectal preparations, oral preparations, injections and buccal preparations.

Described specifically, to formulate the medicinal composition according to the present invention into an intranasal preparation, it is only necessary, for example, to dissolve the peptide, the EO-PO polymer (I), and epsilon aminocaproic acid or tranexamic acid in sterile purified water, to mix the resultant solution with other base and then to adjust its pH to provide an aqueous solution, or to lyophilize the aqueous solution into a powder; or to mix the peptide, the EO-PO polymer (I), epsilon aminocaproic acid or tranexamic acid, and a base in their powder forms.

To formulate the medicinal composition according to the present invention into a rectal preparation, it is only necessary to mix the peptide, the EO-PO polymer (I), epsilon aminocaproic acid or tranexamic acid, and a base into suppositories. These suppositories are not limited to solid to semi-solid ones but the rectal preparation can be formulated in a liquid form. To formulate, for example, an enema which is a liquid preparation, a rectal liquid preparation is formulated in the above-described manner and is then administered by an implement like conventional enemas. In addition, the medicinal preparation according to the present invention, which is in the form of a liquid or a suspension, can be filled in capsules (rectal capsules), followed by administration.

Illustrative of additives usable in the medicinal composition according to the present invention are pH regulators, antiseptics, antioxidants, thickeners, isotonicities, and corrigents. It is also possible to formulate the medicinal composition according to the present invention into so-called lipo preparations such as a water-in-oil emulsion, an oil-in-water emulsion and a liposome by using an appropriate surfactant or the like.

The followings are specific examples of additives usable in the medicinal composition according to the present invention:

pH Regulators

Hydrochloric acid, maleic acid, fumaric acid, acetic acid, citric acid, malic acid, tartaric acid, phosphoric acid, ascorbic acid, salts thereof, and the like.

Antiseptics

Benzalkonium chloride, benzethonium chloride, parabens, benzyl alcohol, and the like.

Thickeners

Polysaccharides, gelatin, cellulose derivatives, polyacrylic acids, macrogols, polyvinyl alcohol, polyvinylpyrrolidone, other high-molecular substances, and the like.

Antioxidants

Vitamin Es, butylhydroxytoluene, butylhydroxyanisole, edetic acids, ascorbic acid, citric acid, propyl gallate, sodium hydrogensulfite, sodium benzoate, sorbitol, sodium thiosulfate, and the like.

Isotonicities

Mannitol, sorbitol, glycerin, glucose, sodium chloride, and the like.

Corrigents

Mentha oil, orange oil, lemon oil, menthol, limonene, vanillin, sweeteners, and the like.

Among the above-described bases, use of citric acid or its salt as a pH regulator is particularly preferred irrespective of the preparation form because, coupled with the action of epsilon aminocaproic acid, it can further promote the absorption.

The excellent peptide-absorption-improving effect of the medicinal composition according to the present invention is considered to promote permucosal or percutaneous absorption of the peptide owing to synergistic effects of the EO-PO polymer (I) and epsilon aminocaproic acid or tranexamic acid.

It was conventionally known to use the ethylene oxide-propylene oxide block copolymer represented by the formula (I) as a surfactant for peptide-containing compositions [Japanese Patent Application Laid-Open (Kokai) No. SHO 63-166832]. Its combined use with epsilon aminocaproic acid is however not disclosed at all, to say nothing of indication of the improved absorption of a peptide owing to their combination.

EXAMPLES

The present invention will next be described in further detail by Examples and Experiments. It is however to be borne in mind that these Examples are merely for illustration and that the present invention shall not be limited at all by them.

Example 1

| Ingredient | Amount |
| --- | --- |
| (1) Salmon calcitonin | 0.026 wt. % |
| (2) Epsilon aminocaproic acid (hereinafter referred to as "EACA") | 0.500 wt. % |
| (3) Ethylene oxide (20) propylene oxide (20) glycol | 1.000 wt. % |
| (4) Mannitol | 4.300 wt. % |
| (5) Benzalkonium chloride | 0.010 wt. % |
| (6) 1N hydrochloric acid | 2.500 wt. % |
| (7) Sterile purified water | 91.664 wt. % |
| Total | 100.000 wt. % |

Example 2

| Ingredient | Amount |
| --- | --- |
| (1) Salmon calcitonin | 0.026 wt. % |
| (2) EACA | 1.000 wt. % |
| (3) Ethylene oxide (25) propylene oxide (30) glycol | 1.000 wt. % |
| (4) Sodium chloride | 0.700 wt. % |
| (5) Benzalkonium chloride | 0.010 wt. % |
| (6) 1N hydrochloric acid | 4.700 wt. % |
| (7) Sterile purified water | 92.564 wt. % |
| Total | 100.000 wt. % |

Example 3

| Ingredient | Amount |
| --- | --- |
| (1) Salmon calcitonin | 0.052 wt. % |
| (2) EACA | 0.500 wt. % |
| (3) Ethylene oxide (160) propylene oxide (30) glycol | 1.000 wt. % |
| (4) Mannitol | 0.500 wt. % |
| (5) Sodium citrate (dihydrate) | 1.237 wt. % |
| (6) Citric acid (monohydrate) | 1.219 wt. % |
| (7) Benzalkonium chloride | 0.010 wt. % |
| (8) Sterile purified water | 95.482 wt. % |
| Total | 100.000 wt. % |

Example 4

| Ingredient | Amount |
| --- | --- |
| (1) Peptide 25* | 0.052 wt. % |
| (2) EACA | 0.500 wt. % |
| (3) Ethylene oxide (20) propylene oxide (20) glycol | 1.000 wt. % |
| (4) Mannitol | 4.300 wt. % |
| (5) Benzalkoniuxn chloride | 0.010 wt. % |
| (6) 1N hydrochloric acid | 2.500 wt. % |
| (7) Sterile purified water | 91.638 wt. % |
| Total | 100.000 wt. % |

Example 5

| Ingredient | Amount |
| --- | --- |
| (1) Peptide 25 | 0.026 wt. % |
| (2) EACA | 0.500 wt. % |
| (3) Ethylene oxide (25) propylene oxide (30) glycol | 1.000 wt. % |
| (4) Mannitol | 4.300 wt. % |
| (5) Benzethonium chloride | 0.010 wt. % |
| (6) 1N hydrochloric acid | 2.500 wt. % |
| (7) Sterile purified water | 91.664 wt. % |
| Total | 100.000 wt. % |

Example 6

| Ingredient | Amount |
| --- | --- |
| (1) Peptide 25 | 0.026 wt. % |
| (2) EACA | 0.500 wt. % |
| (3) Ethylene oxide (160) propylene oxide (30) glycol | 1.000 wt. % |
| (4) Mannitol | 4.300 wt. % |
| (5) Benzethonium chloride | 0.010 wt. % |
| (6) 1N hydrochloric acid | 2.500 wt. % |
| (7) Sterile purified water | 91.664 wt. % |
| Total | 100.000 wt. % |

Example 7

| Ingredient | Amount |
| --- | --- |
| (1) Peptide 25 | 0.026 wt. % |
| (2) EACA | 0.500 wt. % |
| (3) Ethylene oxide (196) propylene oxide (67) glycol | 1.000 wt. % |
| (4) Mannitol | 4.300 wt. % |
| (5) Benzethonium chloride | 0.010 wt. % |

-continued

| Ingredient | Amount |
| --- | --- |
| (6) 1N hydrochloric acid | 2.500 wt. % |
| (7) Sterile purified water | 91.664 wt. % |
| Total | 100.000 wt. % |

Example 8

| Ingredient | Amount |
| --- | --- |
| (1) Peptide 25 | 0.026 wt. % |
| (2) EACA | 0.500 wt. % |
| (3) Ethylene oxide (54) propylene oxide (39) glycol | 1.000 wt. % |
| (4) Mannitol | 4.300 wt. % |
| (5) Benzethonium chloride | 0.010 wt. % |
| (6) 1N hydrochloric acid | 2.500 wt. % |
| (7) Mentha oil | 0.100 wt. % |
| (8) Sterile purified water | 91.564 wt. % |
| Total | 100.000 wt. % |

Example 9

| Ingredient | Amount |
| --- | --- |
| (1) Peptide 25 | 0.015 wt. % |
| (2) EACA | 0.500 wt. % |
| (3) Ethylene oxide (25) propylene oxide (30) glycol | 1.000 wt. % |
| (4) Mannitol | 4.300 wt. % |
| (5) Benzalkonium chloride | 0.010 wt. % |
| (6) 1N hydrochloric acid | 2.500 wt. % |
| (7) Sterile purified water | 91.675 wt. % |
| Total | 100.000 wt. % |

The medicinal compositions according to the present invention, which have been described above in Example 1 to Example 9, can each be used by dissolving the ingredients in the sterile purified water and filling the resultant aqueous solution in an appropriate container. As an alternative, each aqueous solution can be filled in an appropriate container, lyophilized, sealed and then stored. At the time of use, sterile purified water is added to dissolve the lyophilized powder into a solution of an appropriate concentration.

Example 10

| Ingredient | Amount |
| --- | --- |
| (1) EACA | 0.500 wt. % |
| (2) Ethylene oxide (25) propylene oxide (30) glycol | 1.000 wt. % |
| (3) Sodium citrate (dihydrate) | 1.000 wt. % |
| (4) Citric acid (monohydrate) | 1.000 wt. % |
| (5) Hard fat | 96.500 wt. % |
| Total | 100.000 wt. % |

The above formulation is heated and melted into a homogeneous suspension, to which peptide 25 which has been lyophilized in advance together with mannitol in an amount ten times as much as the peptide 25 is added in an amount of 0.00167 wt. %. After the resultant mixture is stirred into a homogeneous mixture, the homogeneous mixture is poured into molds for suppositories and then cooled, whereby suppositories of about 1.5 g each are obtained.

Example 11

| Ingredient | Amount |
| --- | --- |
| (1) EACA | 0.500 wt. % |
| (2) Ethylene oxide (160) propylene oxide (30) glycol | 1.000 wt. % |
| (3) Soybean oil | 10.000 wt. % |
| (4) Purified egg yolk lecithin | 1.200 wt. % |
| (5) Glycerin | 2.500 wt. % |
| (6) Sterile purified water | 84.800 wt. % |
| Total | 100.000 wt. % |

The above formulation is emulsified by a conventional preparation method of fat emulsions for intravenous injection, whereby an emulsion having an average particle size of from 100 nm to 3,000 nm is formed. The emulsion is added with 0.026 wt. % of peptide 25. It is filled in an appropriate container and is then used.

Example 12

| Ingredient | Amount |
| --- | --- |
| (1) EACA | 1.000 wt. % |
| (2) Ethylene oxide (25) propylene oxide (30) glycol | 1.000 wt. % |
| (3) Soybean oil | 10.000 wt. % |
| (4) Purified egg yolk lecithin | 1.200 wt. % |
| (5) Glycerin | 2.500 wt. % |
| (6) Sterile purified water | 84.300 wt. % |
| Total | 100.000 wt. % |

The above composition is emulsified by a conventional preparation method of fat emulsions for intravenous injection, whereby an emulsion having an average particle size of from 100 nm to 3,000 nm is formed. To the emulsion, 0.026 wt. % of peptide 25 was added, followed by dissolution to prepare a composition for pernasal administration.

Example 13

| Ingredient | Amount |
| --- | --- |
| (1) Salmon calcitonin | 0.026 wt. % |
| (2) Tranexamic acid | 0.500 wt. % |
| (3) Ethylene oxide (20) propylene oxide (20) glycol | 1.000 wt. % |
| (4) Mannitol | 4.300 wt. % |
| (5) Benzalkonium chloride | 0.010 wt. % |
| (6) 1N hydrochloric acid | 2.500 wt. % |
| (7) Sterile purified water | 91.664 wt. % |
| Total | 100.000 wt. % |

Example 14

| Ingredient | Amount |
| --- | --- |
| (1) Peptide 25 | 0.052 wt. % |
| (2) Tranexamic acid | 0.500 wt. % |
| (3) Ethylene oxide (25) propylene | 1.000 wt. % |

-continued

| Ingredient | Amount |
|---|---|
| oxide (30) glycol | |
| (4) Mannitol | 4.300 wt. % |
| (5) Benzalkonium chloride | 0.010 wt. % |
| (6) 1N hydrochloric acid | 2.500 wt. % |
| (7) Sterile purified water | 91.638 wt. % |
| Total | 100.000 wt. % |

Example 15

| Ingredient | Amount |
|---|---|
| (1) Peptide 25 | 0.050 wt. % |
| (2) EACA | 2.000 wt. % |
| (3) Ethylene oxide (160) propylene oxide (30) glycol | 10.000 wt. % |
| (4) Hydroxypropylmethylcellulose | 70.000 wt. % |
| (5) Carboxyvinyl polymer | 17.950 wt. % |
| Total | 100.000 wt. % |

The above formulation was compressed by a conventional preparation method for tablets, whereby mucosal adhesive tablets were obtained.

Example 16

| Ingredient | Amount |
|---|---|
| (1) Salmon calcitonin | 0.050 wt. % |
| (2) EACA | 2.000 wt. % |
| (3) Ethylene oxide (160) propylene oxide (30) glycol | 10.000 wt. % |
| (4) Hydroxypropylmethylcellulose | 70.000 wt. % |
| (5) Carboxyvinyl polymer | 17.950 wt. % |
| Total | 100.000 wt. % |

The above formulation was compressed by a conventional preparation method for tablets, whereby mucosal adhesive tablets were obtained.

Experiment 1

Determination of peptide absorption by blood calcium concentration:

Using white male rabbits in groups (5 rabbits per group, Japanese White; body weight: about 2.5 kg) as model animals, an aqueous solution of one of the below-described formulas 1 to 4, said solution having been formulated to give a dose of peptide 25 as much as 15 IU/kg, was administered in an amount of 50 μl to one nasal cavities of the individual rabbits in the corresponding group by a microsyringe. After the administration, blood was periodically sampled from the auricular vein and subjected to centrifugation to collect serum, and the blood calcium concentration was then measured using an atomic absorption spectro-photometer, whereby the absorption of peptide 25 was determined. Peptide 25 is a peptide having calcitonin activity and, when absorbed, lowers the blood calcium concentration. Its measurement therefore permits determination of the absorbability of the peptide.

The results are presented by showing reduction rates of the blood calcium concentration in terms of percentages (%) based on the blood calcium concentration immediately before the administration of the test drug.

Formula 1 (Invention)

The formula of Example 9.

Formula 2 (Comparative Example)

The formulation of Example 9 without EACA and ethylene oxide (25) propylene oxide (30) glycol.

Formula 3 (Comparative Example)

The formulation of Example 9 without EACA.

Formula 4 (Comparative Example)

The formulation of Example 9 without ethylene oxide (25) propylene oxide (30) glycol.

The results are summarized in Table 1.

TABLE 1

| | Time (hr) | | | | | |
|---|---|---|---|---|---|---|
| | 0.5 | 1 | 2 | 3 | 5 | 8 |
| Formula 1 | 7.50 | 9.01 | 9.30 | 9.67 | 5.73 | 6.86 |
| Formula 2 | 4.85 | 6.39 | 4.61 | 4.10 | 3.05 | 3.39 |
| Formula 3 | 4.06 | 5.37 | 4.22 | 3.16 | 2.00 | 3.99 |
| Formula 4 | 3.89 | 4.69 | 4.50 | 4.79 | 0.79 | 3.68 |

It has been proven from the results of Experiment 1 that the medicinal composition according to the present invention (Formula 1), which used epsilon aminocaproic acid and the EO-PO polymer (I) in combination, substantially improves the absorbability of a peptide and also achieve improved prolongation of the effect of the peptide compared with the formulation without both epsilon aminocaproic acid and the EO-PO polymer (I) (Formula 2) or the formulations with one of epsilon aminocaproic acid and the EO-PO polymer (I) (Formulas 3 and 4).

Experiment 2

Determination of Peptide Absorption by RIA Method (Radioimmunoassay)

Using white male rabbits in groups (3 rabbits per group, Japanese White; body weight: about 2.5 kg) as model animals, an aqueous solution of one of the formulas 1 and 2 employed in Test 1, said solution having been formulated to give a dose of peptide 25 as much as 3 IU/kg ug/kg, was administered in an amount of 50 μl to one nasal cavities of the individual rabbits in the corresponding group by a microsyringe.

On the other hand, an injection with 0.8 μg/kg (40 μl dose) of peptide 25 dissolved in the below-described formula was intramuscularly injected as a control to similar rabbits (n=3) as the above-described rabbits. Incidentally, the biological potency of peptide 25 was calculated to be 5000 IU/mg.

| Formula of injection: | |
|---|---|
| Gelatin | 5.00 w/v % |
| Glacial acetic acid | 0.11 w/v % |
| Sodium acetate | 0.05 w/v % |
| D-mannitol | 4.0 w/v % |
| Distilled water (injection grade) | as needed |

After the administration, blood was sampled from the auricular vein periodically upon elapsed times of 10 minutes, 20 minutes, 30 minutes, 60 minutes and 120 minutes and subjected to centrifugation to collect serum samples. The concentrations (pg/ml) of peptide 25 were then measured by the RIA method, and by the below described calculation formula, the bioavailability (%) (hereinafter referred to as "BA") was calculated.

* In the above formula, each AUC indicates the area under the corresponding peptide blood concentration-time curve from 0 minute to 120 minutes.

The results are summarized in Table 2.

TABLE 2

|  | 10 min (pg/ml) | 20 min (pg/ml) | 30 min (pg/ml) | 60 min (pg/ml) | 120 min (pg/ml) | BA (%) |
|---|---|---|---|---|---|---|
| Formula 1 | 44.3 | 215.8 | 225.5 | 136.6 | 56.9 | 14.9 |
| Formula 2 | N. D.* | N. D. | N. D. | N. D. | N. D. | 0 |
| Intra-muscular injection | 500.9 | 491.1 | 403.0 | 301.5 | N. D. | — |

*N. D.: Not detected.

It has been proven from the results of Experiment 2 that the medicinal composition according to the present invention (Formula 1) shows a very high value as BA available by pernasal administration and substantially improves the absorbability of a peptide.

Capability of Exploitation in Industry

As has also become evident in the above-described Experiments, the medicinal composition according to the present invention, which used epsilon aminocaproic acid or tranexamic acid in combination with the EO-PO polymer (I), substantially improved the absorbability of the peptide and also achieved improved prolongation of the effect of the peptide compared with the medicinal compositions which did not use one or both of them.

For the above advantages, the medicinal composition according to the present invention can expand the application range of peptides, such as calcitonin, insulin, interferons and erythropoietin, which have been limited in administration methods and have involved a problem in economy although their effectiveness have been widely acknowledged, and can be advantageously used for the treatment or the like of various diseases such as osteoporosis, hypercalcemia, diabetes, hepatitis and anemia.

We claim:

1. A medicinal composition for permucosal administration comprising a peptide, epsilon aminocaproic acid, and an ethylene oxide-propylene oxide block copolymer represented by the following formula (I):

$$HO(C_2H_4O)_a-(C_3H_6O)_b-(C_2H_4O)_cH \quad (I)$$

wherein a, b and c stand for integers of at least 1, respectively.

2. A medicinal composition for permucosal administration according to claim 1, wherein said ethylene oxide-propylene oxide block copolymer has an HLB of from 5 to 33.

3. A medicinal composition for permucosal administration according to claim 1, wherein said ethylene oxide-propylene oxide block copolymer has an HLB of from 10 to 30.

4. A medicinal composition for permucosal administration according to claim 1, wherein said composition comprises an ethylene oxide-propylene oxide block copolymer in which an average polymerization degree of ethylene oxide is from 10 to 200 and an average polymerization degree of propylene oxide is from 10 to 80.

5. A medicinal composition for permucosal administration according to claim 1, wherein said epsilon aminocaproic acid is incorporated in an amount of from 0.01 wt. % to 10 wt. %.

6. A medicinal composition for permucosal administration according to claim 1, wherein said ethylene oxide-propylene oxide block copolymer is incorporated in an amount of from 0.01 wt. % to 20 wt. %.

7. A medicinal composition for permucosal administration according to claim 1, wherein said epsilon aminocaproic acid is incorporated in an amount of from 0.01 wt. % to 2 wt. % and said ethylene oxide-propylene oxide block copolymer is incorporated in an amount of from 0.01 wt. % to 20 wt. %.

8. A medicinal composition for permucosal administration according to claim 1, wherein said peptide is selected from calcitonin, insulin, a proinsulin, an epidermal growth factor, a growth hormone, somatomedin C, somatostatin, granulocyte macrophage colony-stimulating factor, a colony-stimulating factor, erythropoietin, an interferon, an interleukin, an atrial natriuretic peptide, a parathyroid hormone, a superoxide dismutase, a tissue plasminogen activator, an antithrombin, blood coagulation-factor, protein C, hirudine, hepatitis vaccine, an endorphin, ACTH-releasing hormone, neurotensin, angiotensin, transferrin, endothelin, vasopressin, desmopressin, luteinizing hormone, luteinizing hormone-releasing hormone, prolactin, glucagon, gastrin, secretin, urokinase, vasoactive intestinal polypeptide, hepatitis vaccine, influenza vaccine, pertussis vaccine, diphtheria vaccine or tetanus vaccine.

9. A medicinal composition for permucosal administration according to claim 1, wherein said peptide is calcitonin or insulin.

10. The medicinal composition for permucosal administration according to claim 1, wherein $$10 \leq a+c \leq 200,$$

and $$10 \leq b \leq 80.$$

11. The medicinal composition for permucosal administration according to claim 1, comprising said epsilon aminocaproic acid.

12. The medicinal composition for permucosal administration according to claim 11, wherein $$10 \leq a+c \leq 200,$$

and $$10 \leq b \leq 80.$$

13. A medicinal composition, comprising a peptide, tranexamic acid, and an ethylene oxide-propylene oxide block copolymer represented by formula (I):

wherein a, b and c are each integers having a value at least one.

14. A medicinal composition according to claim 13, wherein said ethylene oxide-propylene oxide block copolymer has an HLB of from 5 to 33.

15. A medicinal composition according to claim 13, wherein said ethylene oxide-propylene oxide block copolymer has an HLB of from 10 to 30.

16. A medicinal composition according to claim 13, wherein said composition comprises an ethylene oxide-propylene oxide block copolymer in which an average polymerization degree of ethylene oxide is from 10 to 200 and an average polymerization degree of propylene oxide is from 10 to 80.

17. A medicinal composition according to claim 13, wherein said tranexamic acid is incorporated in an amount of from 0.01 wt. % to 10 wt. %.

18. A medicinal composition according to claim 13, wherein said ethylene oxide-propylene oxide block copolymer is incorporated in an amount of from 0.01 wt. % to 20 wt. %.

19. A medicinal composition according to claim 13, wherein said tranexamic acid is incorporated in an amount of from 0.01 wt. % to 2 wt. % and said ethylene oxide-propylene oxide block copolymer is incorporated in an amount of from 0.01 wt. % to 20 wt. %.

20. A medicinal composition according to claim 13, wherein said peptide is selected from the group consisting of calcitonin, insulin, a proinsulin, an epidermal growth factor, a growth hormone, somatomedin C, somatostatin, granulocyte macrophage colony-stimulating factor, a colony-stimulating factor, erythropoietin, an interferon, an interleukin, an atrial natriuretic peptide, a parathyroid hormone, a superoxide dismutase, a tissue plasminogen activator, an antithrombin, blood coagulation-factor, protein C, hirudine, hepatitis vaccine, an endorphin, ACTH-releasing hormone, neurotensin, angiotensin, transferrin, endothelin, vasopressin, desmopressin, luteinizing hormone, luteinizing hormone-releasing hormone, prolactin, glucagon, gastrin, secretin, urokinase, vasoactive intestinal polypeptide, hepatitis vaccine, influenza vaccine, pertussis vaccine, diphtheria vaccine and tetanus vaccine.

21. A medicinal composition according to claim 13, wherein said peptide is calcitonin or insulin.

22. A medicinal composition according to claim 13, wherein $$10 \leq a+c \leq 200,$$

and $$10 \leq b \leq 80.$$

* * * * *